US010682081B2

(12) United States Patent
Hirshfield et al.

(10) Patent No.: US 10,682,081 B2
(45) Date of Patent: Jun. 16, 2020

(54) ACQUIRING AND PROCESSING NON-CONTACT FUNCTIONAL NEAR-INFRARED SPECTROSCOPY DATA

(71) Applicant: Outerfacing Technology LLC, Boulder, CO (US)

(72) Inventors: Leanne Hirshfield, Boulder, CO (US); Christopher M. Meier, Lake Mills, WI (US)

(73) Assignee: Outerfacing Technology LLC, Boulder, CO (US)

( * ) Notice: Subject to any disclaimer, the term of this patent is extended or adjusted under 35 U.S.C. 154(b) by 654 days.

(21) Appl. No.: 15/386,488

(22) Filed: Dec. 21, 2016

(65) Prior Publication Data

US 2017/0172479 A1   Jun. 22, 2017

Related U.S. Application Data

(60) Provisional application No. 62/270,332, filed on Dec. 21, 2015.

(51) Int. Cl.
*A61B 5/1455* (2006.01)
*A61B 5/00* (2006.01)

(52) U.S. Cl.
CPC ........ *A61B 5/14553* (2013.01); *A61B 5/0042* (2013.01); *A61B 5/0075* (2013.01); *A61B 5/4064* (2013.01); *A61B 2562/0233* (2013.01)

(58) Field of Classification Search
CPC . A61B 5/14553; A61B 5/4064; A61B 5/0042; A61B 5/0075; A61B 2562/0233
See application file for complete search history.

(56) References Cited

U.S. PATENT DOCUMENTS

| | | | | |
|---|---|---|---|---|
| 2006/0007343 A1* | 1/2006 | Thomas | | G01J 3/36 348/336 |
| 2006/0058683 A1* | 3/2006 | Chance | | A61B 5/0059 600/476 |
| 2011/0208063 A1* | 8/2011 | Papazoglou | | A61B 5/0059 600/473 |
| 2017/0164830 A1* | 6/2017 | Huang | | G06T 7/13 |
| 2017/0319114 A1* | 11/2017 | Kaestle | | A61B 5/0077 |

* cited by examiner

*Primary Examiner* — Eric F Winakur
*Assistant Examiner* — Abid A Mustansir
(74) *Attorney, Agent, or Firm* — Heslin Rothenberg Farley & Mesiti P.C.; Rachel L. Pearlman, Esq.

(57) ABSTRACT

A method, system, and computer program product include aiming a light source at an object, where the light source is communicatively coupled to the processor, and where the light source and the image capture device are both positioned at pre-defined distances from a the object and are not in contact with the object. The processor enables the image capture device, to capture measurements of reflected light, where the reflected light comprises the light from the source as the light is reflected out of the object, where the image capture device is communicatively coupled to the processor, and where an image comprises the measurements. The processor obtains the image and locates data indicating a center of the light source in the image. The processor extracts intensities of the reflected light at a pixel location measured to be a predefined distance from the center of the light source in the image.

18 Claims, 10 Drawing Sheets

ACQUIRING AND PROCESSING NON-CONTACT FUNCTIONAL NEAR-INFRARED SPECTROSCOPY DATA

CROSS-REFERENCE TO RELATED APPLICATIONS

This application claims priority to U.S. Provisional Application No. 62/270,332 filed Dec. 21, 2016, entitled, "ACQUIRING AND PROCESSING NON-CONTACT FUNCTIONAL NEAR-INFRARED SPECTROSCOPY DATA GENERATION OF MULTIPLE LOW-NOISE COPIES OF OPTICAL SIGNALS" which is incorporated herein by reference in its entirety.

STATEMENT OF GOVERNMENT RIGHTS

The invention was made with government support under Contract No. FA-8650-09-D-6939 awarded by the Air Force Research Laboratory (AFRL). The government has certain rights in the present invention.

BACKGROUND

Recent advancements in biotechnology have resulted in brain measurement devices that can non-invasively measure the functioning brain in people's natural environments. Functional Near-Infrared Spectroscopy (fNIRS) is such a technique, which measures the hemoglobin signatures related to neural activation. With the potential to monitor people's mental states non-invasively and in real-time, researchers have used head-mounted fNIRS devices to measure a myriad of cognitive and emotional states in operational settings.

BRIEF SUMMARY

Shortcomings of the prior art are overcome and additional advantages are provided through the provision of acquiring and processing non-contact functional near-infrared spectroscopy data. The method includes, for instance: aiming a light source at an object, wherein the light source is communicatively coupled to a processor, wherein where the light source are positioned at predefined distances from the object such that the light source and the image capture device are not in direct contact with the object; enabling, by the processor, the image capture device, to capture measurements of reflected light, wherein the reflected light comprises the light from the light source as the light is reflected out of the object, wherein the image capture device is communicatively coupled to the processor, and wherein an image comprises the measurements; obtaining, by the processor, from the image capture device, the image; locating, by the processor, in the image, data indicating a center of the light source in the image; and extracting, by the processor, intensities of the reflected light at a pixel location measured to be a predefined distance from the center of the light source in the image.

Computer systems and computer program products relating to one or more aspects of the technique are also described and may be claimed herein. Further, services relating to one or more aspects of the technique are also described and may be claimed herein.

Additional features are realized through the techniques of the present invention. Other embodiments and aspects of the invention are described in detail herein and are considered a part of the claimed invention.

BRIEF DESCRIPTION OF THE SEVERAL VIEWS OF THE DRAWINGS

One or more aspects of the present invention are particularly pointed out and distinctly claimed as examples in the claims at the conclusion of the specification. The foregoing and objects, features, and advantages of one or more aspects of the invention are apparent from the following detailed description taken in conjunction with the accompanying drawings in which:

DETAILED DESCRIPTION

Figure 1:
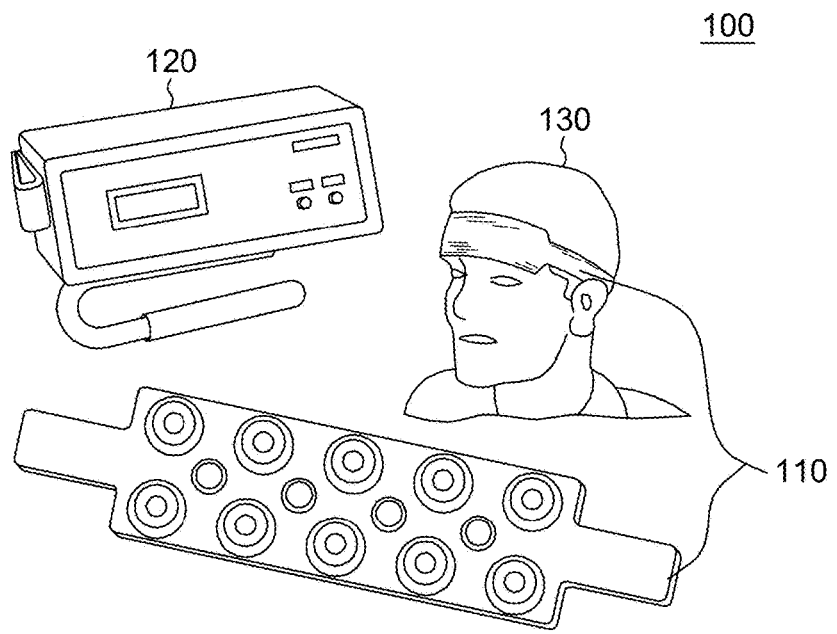
FIG. 1 depicts aspects of a traditional fNIRS system.

The accompanying figures, in which like reference numerals refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures. It should be understood that the Figures are merely schematic and are not drawn to scale.

As understood by one of skill in the art, program code, as referred to throughout this application, includes both software and hardware. For example, program code in certain embodiments of the present invention includes fixed function hardware, while other embodiments utilized a software-based implementation of the functionality described. Certain embodiments combine both types of program code.

Embodiments of the present invention provide a method of measuring functional brain activity of a subject without having an apparatus in contact with the subject, i.e., in a non-contact manner. Specifically, embodiments of the present invention may be utilized to measure fNIRS data, including, but not limited to, change in -oxy, -deoxy-, and total blood flow, in the brain. Embodiments of the present invention utilize a light source (e.g., a laser), and one or more image capture device(s) (e.g., a camera). The light source in embodiments of the present invention is utilized to point light at a subject with brain activity, and the image capture device is utilized to capture the reflected light. The data obtained by the image capture device is processed by program code executed by a processor that is communicatively coupled to the image capture device. Based on the data received by the image capture device, the program code produces information regarding the change in -oxy, -deoxy-, and total blood flow, in the brain of the subject. In embodiments of the present invention, the wavelengths of the light from the light source and the distance of the object from the light source and/or the image capture device assist in enabling the program code to ultimately provide the aforementioned fNIRS data.

The basis of functional near-infrared spectroscopy (fNIRS) is the usage of near-infrared light, which can penetrate the scalp and skull to reach the brain cortex. The "f" for "functional" signifies the capability to measure the "functional" human brain, which involves hemoglobin flowing to specific brain regions, based on the neural activation in that region needed to complete a given information processing task. In existing fNIRS devices, optical fibers are placed on the surface of the head for illumination, pulsing near infrared light into the head, and detection fibers are placed on the head to measure light which reflects back (see, e.g., FIG. 3). Due to the scattering nature of tissue, light reflecting back out of the head which is measured at a greater distance from the illumination point has traveled deeper into tissue than reflected light measured at a closer distance to the illumination point (see, e.g., FIG. 3). Typically, in these existing systems, detection fibers are placed ~3 cm away from the source fiber to guarantee that light has gone deep enough into the head to interact with brain tissue. Since two wavelengths of light are typically used in the near-infrared wavelength range (650-850 nm), spectral features of hemoglobin can be measured. Particularly, concentration changes in oxy- and deoxy-hemoglobin can be distinguished, which are directly related to brain activation.

Embodiments of the present invention offers advantages over these existing systems because these embodiments, which can be referred to as remote fNIRS, provide for fNIRS measurements to be taken from a distance, rather than requiring direct contact with the head. Embodiments of the present invention enable remoted functionality in part by placing light sources some distance away from the head, and using these sources to pulse near-infrared light at two wavelengths (e.g., 685 and 830 nm) onto the head, creating a light insertion point. In an embodiment of the present invention, one or more image capture devices, such as specialized cameras, are placed at some distance from the head in order to take images of the skin surrounding the light insertion point. These cameras play the role of the "light detector" in existing fNIRS devices in that the cameras take images of the light insertion point and the skin surrounding the insertion point. One or more programs utilize the image data from the cameras to measure the light intensity values at pixels in the image that are located at specific distances (e.g., ~3 cm) from the center of the light insertion point in order to act as a light detector (see, e.g., FIG. 7). Since an image of a light insertion point has many pixels surrounding the insertion point, an advantage of embodiments of the present invention over existing systems is that remote-fNIRS has the capability to create many light detectors, resulting in many areas of the brain being measured (see, e.g., FIG. 9). Traditional fNIRS devices measure one brain location each one source-detector pairing (see, e.g., FIG. 3). Expensive photomultiplier tubes are used for the light detectors, making fNIRS devices increase dramatically in price as the number of detectors are increased. Embodiments of the present invention do not share this constraint. In embodiments of the present invention, one or more programs locates the center of the light source in the images and extracts the reflected light intensities (e.g., 685 nm and 830 nm) at a pixel location measured to be 3 cm from the center of the light source in the image (see, e.g., FIG. 7).

Figure 8:
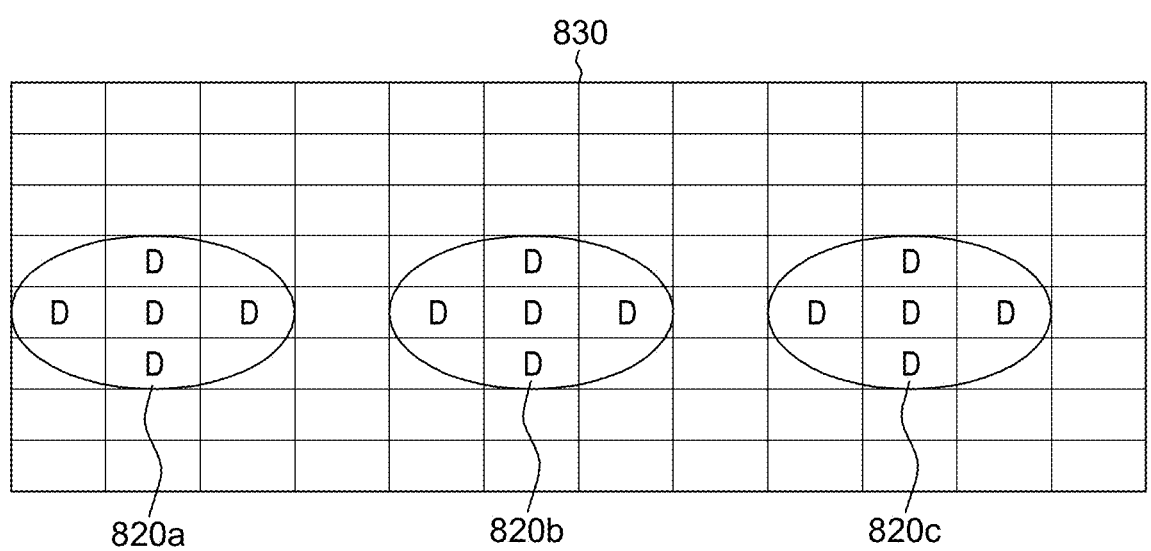
FIG. 8 depicts the creation of multiple detectors, in accordance with an embodiment of the present invention.

By looking at different distances from the source insertion point, it is possible to create multiple detectors, resulting in multiple source-detector pairings. Each source-detector pairing results in a new channel of data, enabling us to measure another area of the brain (FIG. 8). By extracting light intensity values from different pixels in the image, embodiments of the present invention effectively create "detectors" all around a light source insertion point. Thus, unlike existing head mounted fNIRS systems, which include new photomultiplier tubes for each new detector, in embodiments of the present invention, the one or more programs can add detectors by extracting light from different regions of the image. In one non-limiting example, utilizing this approach, embodiments of the present invention collect channels of data in a 3.5 cm radius surrounding the source insertion point, where the program code can create a new channel of data (source-detector pairing) for each pixel in the 3.5 cm radius surrounding the insertion point. In addition to getting many channel locations of brain data through these source-detector pairings, embodiments of the present invention also use different distances of source-detector pairings to remove noise in the cognitive fNIRS signal.

An advantage of certain embodiments of the present invention is that the fNIRS data is collected without requiring an apparatus that is in contact with the subject from which the data is collected. Certain embodiments of the present invention enable data collection from distances greater than 1 meter, not just a few centimeters from the skin of the subject.

An advantage of certain embodiments of the present invention is that the images that are captured by one or more image capture devices are utilized by the program code such that the processor obtains, in a given image, many detectors from each pixel. As aforementioned, by extracting light intensity values from different pixels in the image, embodiments of the present invention effectively create "detectors" all around a light source insertion point. The multiple detectors enable the program code to make many source-detector pairings, where a source-detector pairing results in a new area of the brain being measured (i.e., a new channel of data). This aspect provides a number of advantages, including: 1) embodiments of the present invention obtain more channels of data with less equipment and at a lower cost than head-mounted fNIRS (which will be discussed later); and 2) the concurrent channel measurements enable measurement of a relatively large (e.g., 3.5 cm radius) region of different scalp, skull, and brain regions per light source, providing more information per light source than has been achieved in previous apparatuses and/or any combination of detectors, in head mounted fNIRS devices. Thus, embodiments of the present invention provide more information about brain and physiological data than can be provided with head mounted fNIRS.

Head-mounted fNIRS devices measure relative changes in oxygenated, deoxygenated, and total blood flow in the brain. Some embodiments of the present invention include a non-contact fNIRS method, that when utilized, enables these same measurements to be made from a distance, without contact. Some embodiments of the present invention can measure relative changes in oxygenated, deoxygenated, and total blood flow in the brain at distances of up to 0.6 meters. This distance is offered as an example as further embodiments of the present invention can measure from greater and lesser distances. Current head-mounted fNIRS devices work with light sources pulsing light at two wavelengths (e.g., between 650 and 850 nm) into the head and they include powerful light detectors to pick up the light at these wavelengths that is reflected back out of the head, where a pairing between one source and one detector measures one area of the brain, often called a channel. Unlike current head-mounted fNIRS, embodiments of the present invention achieve non-contact measurements by using light sources placed away from subjects and one or more image capture device(s), including but not limited to, a specialized camera that produces images where the pixels in the image can be used to create many light detectors, resulting in many source-detector pairings that can measure many regions (also called channels) of the brain concurrently. Program code executing on at least one processor obtains the resulting images and produces measurements of the rate of change in oxy- deoxy-, and total blood flow, as is done by continuous wave head-mounted fNIRS devices.

An advantage of a non-contact fNIRS system, which is integrated into some embodiments of the present invention, is that when compared to contact systems, a non-contact system allows for fNIRS information to be acquired without the cumbersome process of wearing bulky sensors on the head. A further advantage of certain embodiments is that they involve less equipment per measurement location and are therefore less expensive than current contact systems. For example, commercial head-mounted fNIRS systems are expensive because of the cost of their powerful light detectors. Embodiments of the present invention do not include these light detectors. Rather, by using the camera as a light detector, embodiments of the present invention can use an image from the camera to mimic many light detectors (every pixel in the image could theoretically be a detector where information about light intensity can be extracted from). Since each source-detector pairing results in a new region of the brain being measured (a new "channel" of data measuring an additional region of the brain), the present invention reduces the need for many light detectors, using one camera to mimic the functionality of multiple light detectors.

An advantage of certain embodiments of the present invention is that by utilizing a non-contact fNIRS, one or more programs can acquire measurements at a distance, without requiring direct contact with the head. The capability to measure brain activation from a distance is valuable in a number of applications, including, but not limited to those described herein.

Some embodiments of the present invention may be utilized to monitor personnel without the need for cumbersome sensors, in order to measure the neural correlates related to a range of psychological states such as cognitive load, trust, suspicion, complacency, and frustration.

Some embodiments of the present invention may be utilized for monitoring sensitive populations (e.g., patients with mental illness, traumatic brain injury (TBI), or post-traumatic stress disorder (PTSD), etc.) in a manner that would eliminate the discomfort of wearing constricting sensors on the head. Embodiments of the present invention that include mobile, hand-held non-contact fNIRS devices take these measurements in a range of operational settings.

Some embodiments of the present invention include helmets, hats, and augmented and virtual reality displays (e.g., Google Glass®, Oculus Rift®, Microsoft Vive®) embedded with a camera and light source add-on that enables unobtrusive continuous brain measurement without requiring sensor contact with the head.

Some embodiments of the present invention may be integrated into scanners at high security entry control points (ECP's) venues such as airports to increase the security of these environments. Specifically, these control points can be equipped with remote fNIRS sensors to search for neural correlates of deception, anxiety, and/or other signs of mal-intent from people passing through.

Figure 2:
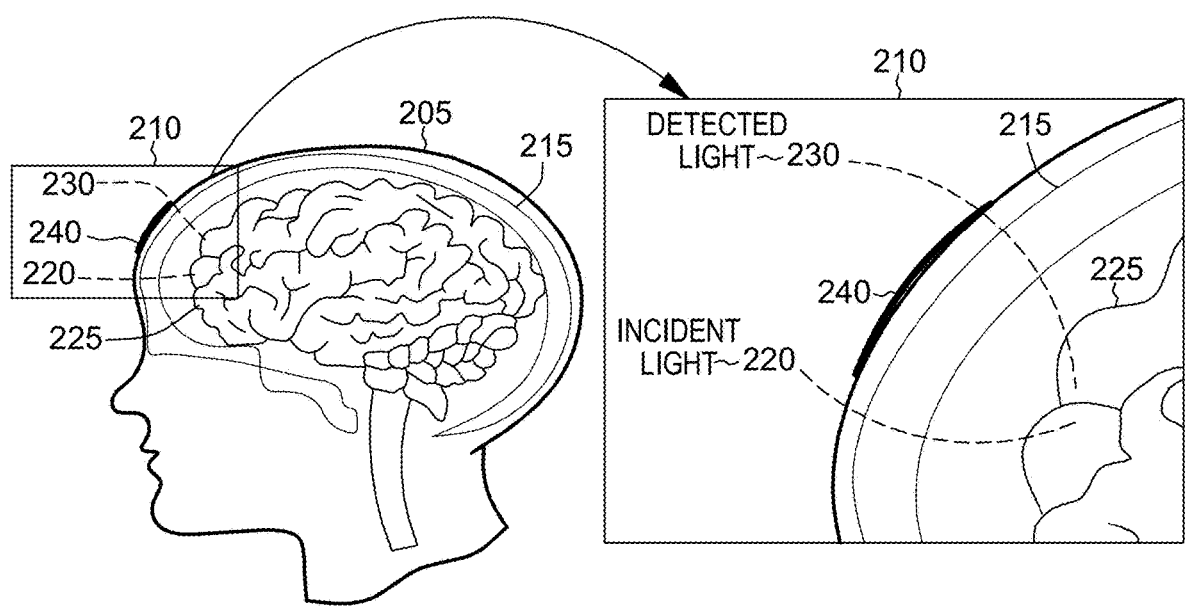
FIG. 2 illustrates certain aspects of present fNIRS systems and methods.
Figure 3:
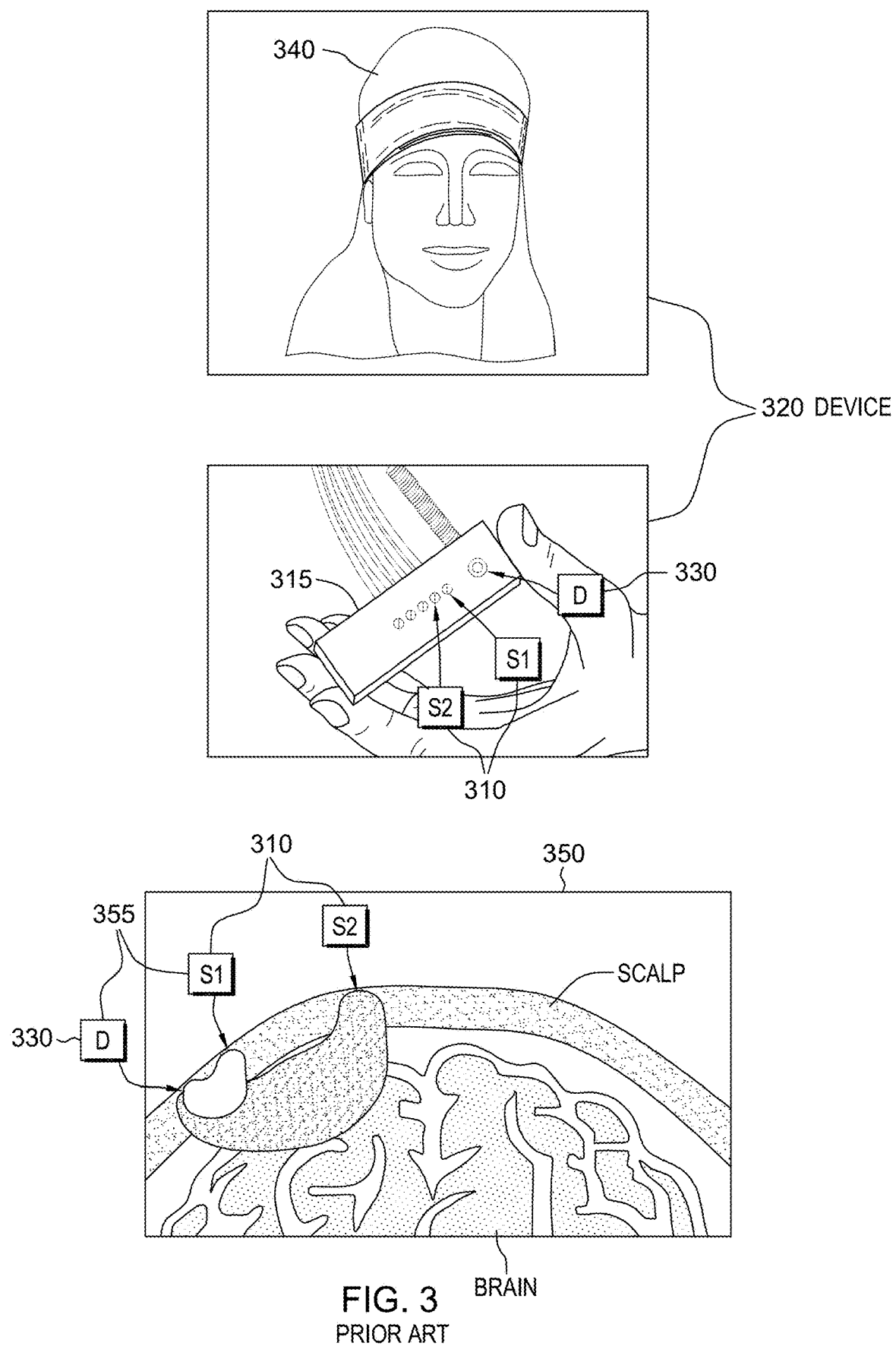
FIG. 3 depicts aspects of a traditional fNIRS system.

FIGS. 1-3 depict various aspects of existing systems and methods that utilize fNIRS. FIG. 1 depicts aspects of a traditional fNIRS system, i.e., a contact fNIRS system). FIG. 2 demonstrates certain aspects of present fNIRS systems and methods. FIG. 3 also depicts aspects of a tradition fNIRS system, i.e., a contact fNIRS system.

As seen in FIG. 2, fNIRS uses near-infrared light, which can penetrate through scalp 205 and skull 215 and reach the brain cortex 225 of an individual 205. Optical fibers are placed on the surface of the head for illumination and detection fibers to measure light which reflects back. Due to the scattering nature of tissue, light which is measured at a distance from the illumination point has traveled deeper into tissue. As seen in FIG. 2, the incident light 220, enters at a portion of the scalp 240 of an individual 205 and is detected as detected light 230 exiting nearby after penetrating the scalp 205, skull 215, and reaching the bran cortex 225.

In existing systems that utilize fNIRS, such as the system 100 shown in FIG. 1, detection fibers are placed ~3 cm away from the source fiber to guarantee that light has interacted with brain tissue. As aforementioned, an individual 130 wears a in a channel sensor apparatus 110 that is coupled (not shown) to a control box 120, which can be referred to as a continuous wave NIR spectroscopy (NIRS) control box 120. In one example, this control box 120 includes pin connectors to provide channels, and a USB cable. The channel sensor apparatus 110 includes sources and detectors. Since two wavelengths of light are typically used in the near-infrared wavelength range (650-850 nm), spectral features of hemoglobin can be measured. Particularly, concentration changes in oxy- and deoxy-hemoglobin can be distinguished. Due to neuro-vascular coupling, changes in hemoglobin concentration can be used for measuring the vascular effect of brain activation.

An example of a commercial fNIRS device is the ISS OxiplexTS®, which is depicted in FIG. 3. The device in FIG. 3 includes a probe that has a detector and four light sources. Each light source produces near-infrared light at two wavelengths (690 nm and 830 nm) which are pulsed intermittently in time. This results in the probe measuring 4 light sources×2 wavelengths=8 readings at each time point. A 'channel' is the measurements taken by a given source-detector pairing.

Referring to FIG. 3, an example of a current contact fNIRS device 320 is depicted on the left with the light sources and detectors embedded into a rubber probe 315. A detector and set of light sources 310 (s1, s2, s3, and s4, two of which are highlighted as S1 and S2) are placed on the head 340. On the right of FIG. 3 is a schematic 350 showing the differences in penetration depths between the two source-detector separation distances. A detector 330, labeled also as D, is also seen in FIG. 3.

In the example in FIG. 3, when viewing a source S1 and detector 330 pairing on the scalp, the location of the "channel" measurement is at the midpoint between the source S1 and detector 330. The source-detector pairings that are farther away from one another result in deeper measurements. The closer source-detector pairings S1-D 355 do not reach the brain, but they can be very useful for identifying other physiological measurements such as heartrate and respiration.

Figure 4:
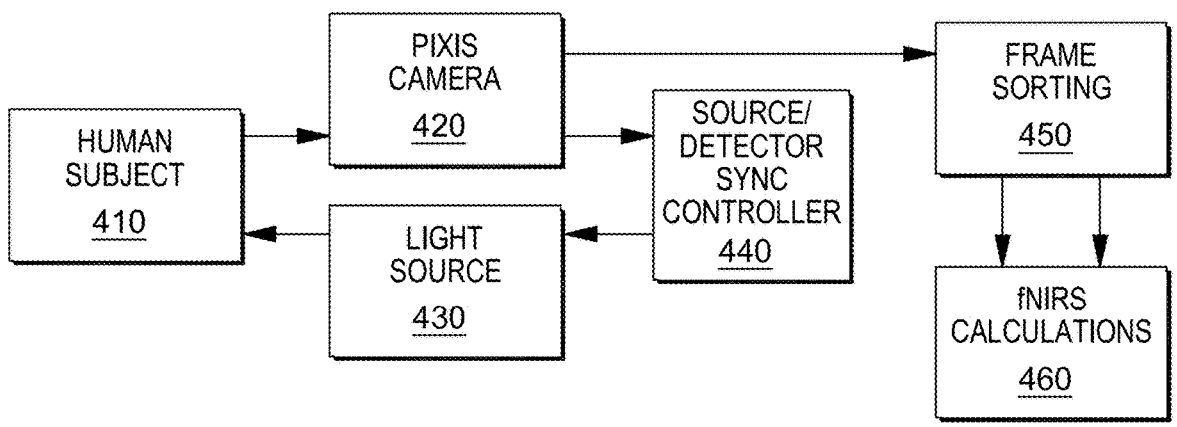
FIG. 4 depicts a schematic that includes aspects of some embodiments of the present invention.

Embodiments of the present invention include an fNIRS configuration that does not necessitate or utilize contact in the manner of the traditional systems depicted in FIGS. 1 and 3. For ease of understanding, the non-contact aspect of embodiments of the present invention will be referred to as non-contact fNIRS or nc-fNIRS. FIG. 4 depicts a schematic that includes aspects of some embodiments of the present invention. FIG. 4 depicts an examples of pulsating single source detection in accordance with an embodiment of the present invention.

Some embodiments of the present invention include the ability to measure changes in sampled light intensities over time with a high level of confidence. To ensure that the decreased intensity of light over a distance was measureable, some embodiments of the present invention utilize a sensor that is sensitive to the wavelengths of interest (650-850 nm). Thus, some embodiments of the present invention utilize a CCD technology that increases the quantum efficiency (QE) in the NIR bands to ~70% by sampling light from the backside of a thickened CCD sensor, referred to as deep-depletion. One example of such a technology is The Princeton Instruments PIXIS 512B imager (depicted in FIG. 4), a cooled-deep depletion CCD with a mechanical shutter and 16-bit analog to digital converter. The mechanical shutter ensures that light from the previous frame does not "bleed into" subsequent frames.

As seen in FIG. 4, an embodiment of the present invention also includes a light source 430. To provide a non-limiting example, FIG. 4 depicts the ThorLabs MCLS-1 Multiple Channel Laser to supply the light sources for the embodiment pictured. In an embodiment of the present invention, two wavelengths were chosen, 690 nm and 830 nm, as those wavelengths are typically used for oxy-, deoxy-, and total hemoglobin measurements in the brain. Furthermore, in an embodiment of the present invention, the light source 430 accepts a hardware modulation signal or serial commands from one or more programs through a USB, which allows us to either modulate the light sources at a given frequency or multiplex the two sources. Thus, one or more programs of a source/detector synchronization controller 440 can send modulation signal or serial commands to the light source 430.

In an embodiment of the present invention, the operation of the light source 430 can be manipulated through this hardware modulation line to turn on/off each of the sources, alternately. Using the same pulse source, the source/detector synchronization controller 440, the PIXIS device 420 can be triggered by one or more programs executing at this source to collect an image, where the image contains the wavelength of interest.

In an embodiment of the present invention, program code executing on a processor enables a working nc-fNIRS that pulses the light sources 430 (e.g., 690 nm and 830 nm) and takes pictures at the correct syncing rate to collect measurements of these light sources as they are reflected out of a material (e.g., an arm or head), the human subject 410. The program code locates the center of the light source in the images and extracts the reflected light intensities (e.g., 690 nm and 830 nm) at a pixel location measured to be a predefined distance from the center of the light source in the image. In an embodiment of the present invention, the predefined distance is 3 cm.

As illustrated in the FIG. 4, one or more programs determines that an image capture device (e.g., a camera) 420 is acquiring a series of images of reflected light of a light source 430 off of a human subject 410 and based on this determination, one or more programs in a sync controller 440 alternate the wavelengths produced by a light source 430 (405). Based on the alternative wavelengths, one or more programs acquire from the image capture device 420, images as a series of alternating wavelength images (415). The one or more programs assembles intensity signals for each wavelength (425). One or more programs provide frame sorting 450 and calculations 460.

Although FIG. 4 utilizes a PIXIS camera 420, additional embodiments of the present invention utilize different cameras or image capture devices to provide a light source, as previously described. A more cost-efficient embodiment of the present invention in depicted in FIG. 5 and includes two CMOS cameras. CMOS camera pod 520, where each camera is configured to measure a different light intensity, in the example provided, either the 690 nm or the 830 nm light intensities, enabling the wavelengths of light to be multiplexed rather than modulated. This embodiment of the present invention provides a dual band source and dual imager. These imagers are much lower cost and have a smaller footprint than the relatively large and cumbersome PIXIS camera. Each imager with lens is ~4×2×2 inches, while the PIXIS is >8×4×4 inches. While they are lower in sensitivity and in bit depth, the program code in an embodiment of the present invention may obtain fNIRS data through signal processing.

Figure 5:
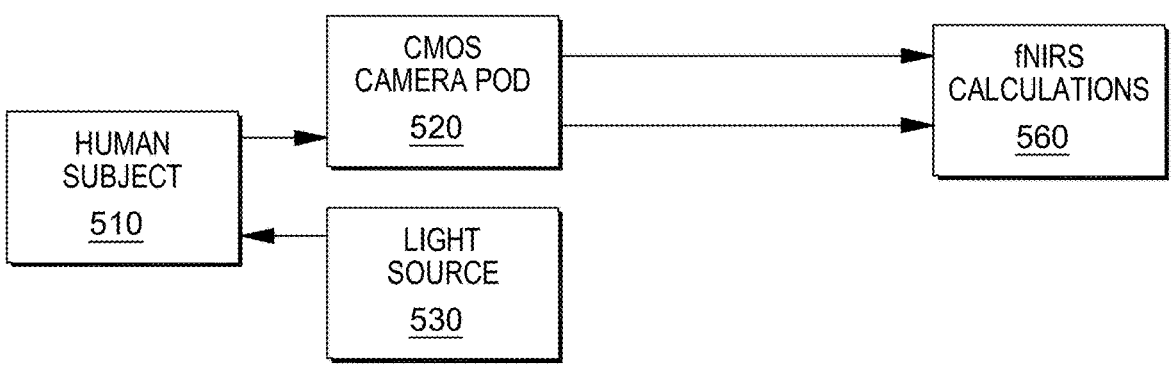
FIG. 5 depicts one or more aspects of an embodiment of the present invention.

As in FIG. 4, in FIG. 5, an image capture device, in this embodiment, CMOS camera pod 520, captures images of light from a light source 530 reflected off a human subject 510. The light source 530 in this embodiment provides continuous source illumination, so no synchronization is utilized. The CMOS camera pod 520, acquires both wavelengths from the same image (that it captures). Thus, utilizing a CMOS camera pod 520 as an image capture device doubles the sampling rate and allows optimization of detector to wavelength.

As will be discussed later, to collect fNIRS data without making contact with a subject, light sources are utilized in embodiments of the present invention in configurations both as alternating coherent light sources and as continually illuminating the subject. Some embodiments of the present invention 600 include alternating coherent light sources (e.g., one source at 685 nm and one at 830 nm) and some embodiments of the present invention include one dual band coherent light source (e.g., 685 nm and 830 nm sources coupled together into the same optical path). The light sources are not pulsed in either embodiment. In the alternating configuration, a frame-to-wavelength synchronization device alternates the coherent light sources such that only one wavelength is present in a given image. After the program code collects the images (each frame alternates what information it carries) the program code sorts the frames processes them to create the fNIRS signals. This configuration may include a single image capture device (e.g., camera). In the continually illuminating configuration, two cameras acquire images. This configuration may include a dichroic mirror that splits the optical paths such that, e.g., the 685 nm light and 830 nm light information go to their respective cameras. The use of the mirror removes the need for a frame-to-wavelength synchronization device. The program code processes the images from each camera independently to gain raw intensity images that it can then process to create the fNIRS signals.

Figure 6:
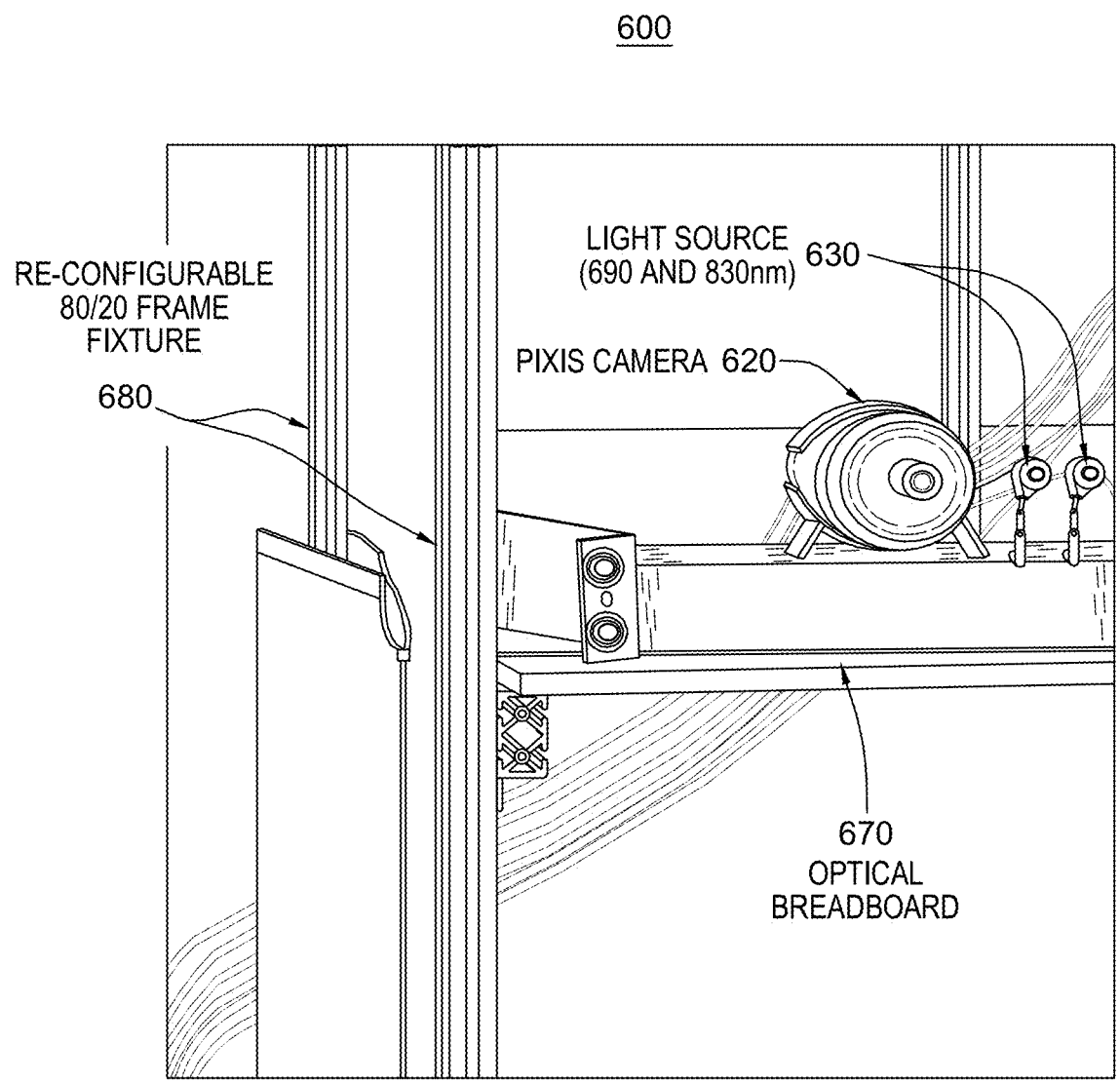
FIG. 6 depicts one or more aspects of an embodiment of the present invention.

As illustrated in FIG. 6, some embodiments of a Non Contact Functional Near-Infrared Spectroscopy (nc-fNIRS) system, method, and computer from product a point coherent photon source 630 for two differing wavelengths (e.g., 690 nm and 830 nm). In an embodiment of the present invention, these aforementioned wavelengths may be chosen according to the optical window for the imaging of oxygenated and deoxygenated hemoglobin. As aforementioned, in an embodiment of the present invention, these wavelengths are 685 nm and 830 nm. As understood by one of skill in the art, other wavelengths can be used given that there is proper sensitivity in the imaging device to detect the small changes in that wavelength. In an embodiment of the present invention, one wavelength has a higher absorption/transmission/reflection coefficient for oxygenated hemoglobin and the other has a higher absorption/transmission/reflection coefficient for deoxygenated hemoglobin. As seen in FIG. 6, this embodiment of the present invention utilizes a PIXIS camera 620 is the image capture device. This embodiment of the present invention also include a re-configurable 80/20 frame fixture and an optical breadboard 670 that secure the elements in the setup.

In an embodiment of the present invention, the light source is applied in an area where a sufficient distance between the point of innervation into the tissue and the maximum distance to measure the depth of the cortical tissue to measure (referred to from now on as the insertion point). In an embodiment of the present invention, the distance is at least 4 cm, but varies in different embodiments based on depth penetration and/or the limits of an imager's ability to measure changes in light intensities.

A sufficient distance refers to an operable distance. As understood by one of skill in the art, fNIRS in the described state relies on back reflected/refracted light. The light innervates the tissue at a location where the source to detection distance is operable. To measure the deep tissue, one centers the source detector pair over the location, thus the source location and detector location cannot be blocked. The concept is further illustrated in FIGS. 2-3.

A sufficient distance, as described above is a distance between a source-detector pairing sufficient to reach a depth, i.e., order to reach the brain, you need to have enough distance between a source-detector pairing. In an embodiment of the present invention, the same distances used by traditional fNIRS can be utilized, including but not limited to: a 3 cm distance between the source and detector, to be sure the brain has been reached. In this embodiment, the light source is applied on an area of the forehead where one can measure 3 cm away from that to measure light intensity in a pixel (i.e., the detector). In this example, if a camera is not set up to capture the region 3 cm away, the setup would not function appropriately. Thus, in an embodiment of the present invention includes enough space around an insertion point to enable measurement of the light intensity at a location ~3 cm away, which would be the detector. In this example, 3 cm is the "sufficient distance."

In an embodiment of the present invention, the point-sources can be either alternately pulsed in synchrony with the camera's frame acquisition, or each point-source can constantly illuminate the tissue. If the point sources are not pulsed a system of dichroic mirrors or prisms can be used to separate the light paths such that information carried by one wavelength is imaged by only one imager.

In an embodiment of the present invention, the program code obtains pixel per distance metric measurements, which are determined either through distance mapping or through stereopsis calibration of multiple imagers.

The quality of the nc-fNIRS data, like many acquisition systems, depends in part on the sensitivity of the ability to measure the data of interest. Traditional fNIRS devices use photomultiplier tubes to increase the signal to noise ratio of the acquisition, however photomultiplier tubes only measure a single point or area without resolution of direction. Some embodiments of the present invention provide an advantage over these traditional setups because they do not require image intensifier tubes or special imaging sensors, however, some embodiments of the present invention incorporate these technologies to increase the quality and depth of penetration of the nc-fNIRS and SNR.

Figure 13:
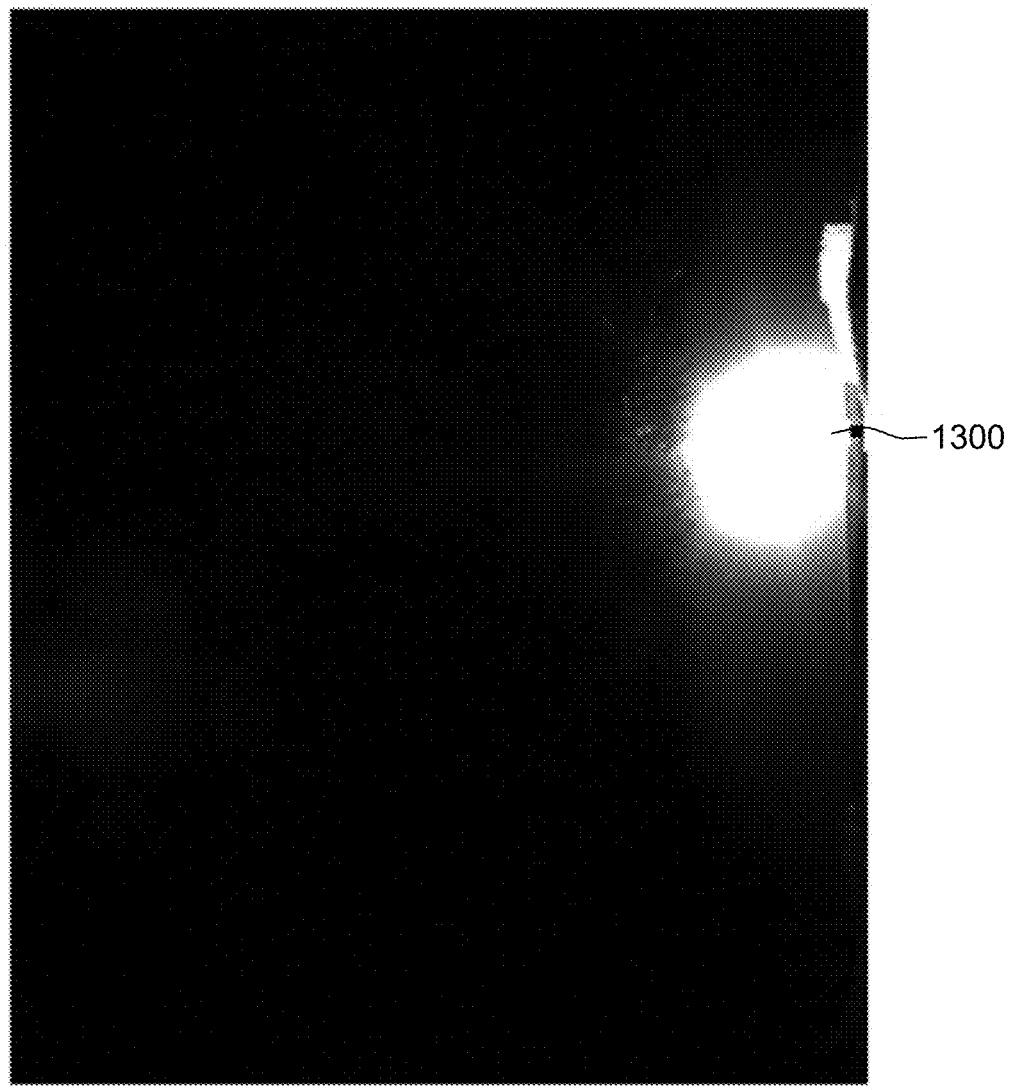
FIG. 13 is an image taken of a light insertion point.

In an embodiment of the present invention, an image/video acquisition device acquires a video image of an area around the insertion point, including the insertion point. FIG. 13 shows an example of an image with a light insertion point. The program code executing on a processor applies an insertion point detection algorithm that uses oval and blob detection techniques and pixel per distance metrics to find the source-insertion point in the image, and to create a distance grid on the image. FIG. 13 is an image taken of a light insertion point 1300.

Figure 7:
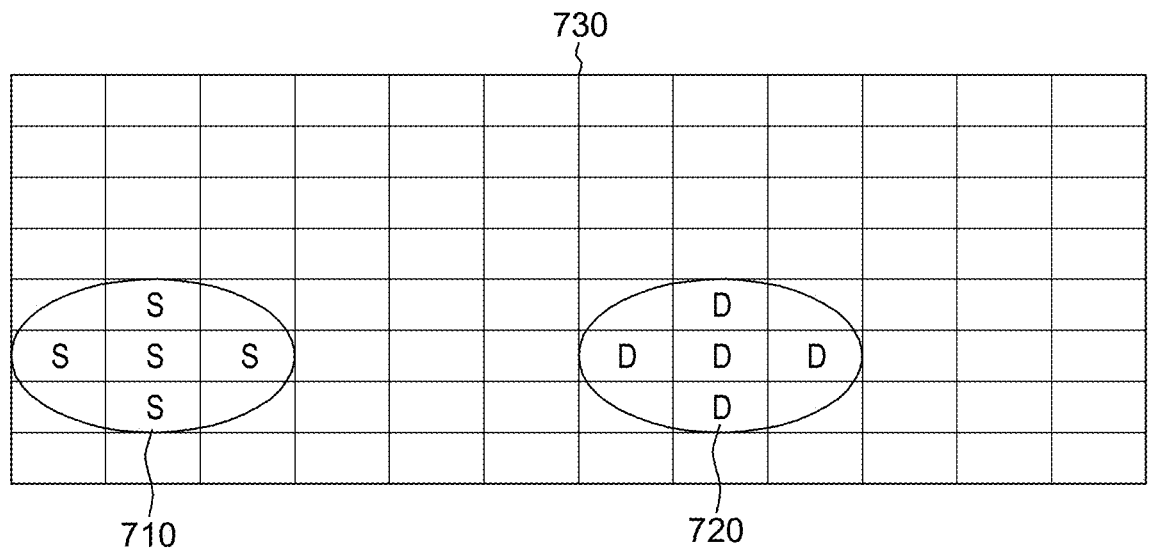
FIG. 7 is an example of a distance map, which is utilized by one or more aspects of an embodiment of the present invention.

FIG. 7 is an example of a distance map, showing an image as grid of sensors, which is utilized by the program code, in an embodiment of the present invention, to create a map of coefficients for the modified Beer-Lambert Law to utilize to obtain fNIRS data. As illustrated in FIG. 7, program code obtains an image from the camera and automatically finds the center of the light insertion point (source). The program code utilizes algorithms, including those described herein, to locate the point. The ability of the program code to find the center enables different embodiments to operate at specific distances from the source insertion point to extract light intensity, and thus, create a light detector.

As illustrated in FIG. 7, if the source innervates a subject 730 at a first point 710 comprised of source pixels, one or more programs can measure an area of pixels at a second point 720, comprised of detector pixels. A circular or cross pattern is shown, although FIG. 7 demonstrates this functionality with a rectangular area as the second point 730.

FIG. 8, also showing an image as grid of sensors, depicts how the program code can create multiple detectors, in accordance with an embodiment of the present invention. As aforementioned, the program code can create a light detector. By looking at different distances from the source insertion point, the embodiment of the present invention comprises multiple detectors, resulting in multiple source-detector pairings. Each source-detector pairing results in a new channel of data, enabling the program code that ultimately receives data to potentially measure another area of the brain of a subject. Each source-detector pairing resulting in a new channel of data. The three points 820a-820b become three simultaneously sampled regions at three different distances. In contrast to existing fNIRS devices, such as the ISIS device, which creates four samples for each wavelength, embodiments of the present invention create one sample for each wavelength.

Figure 9:
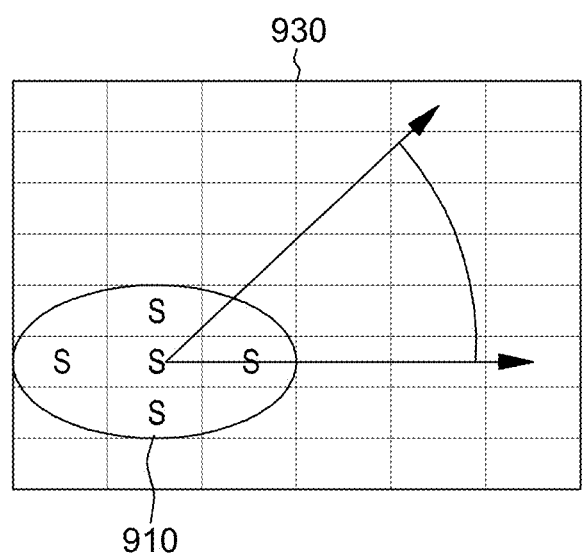
FIG. 9 depicts the creation of many detectors around a light source insertion point, in accordance with an embodiment of the present invention.
Figure 12:
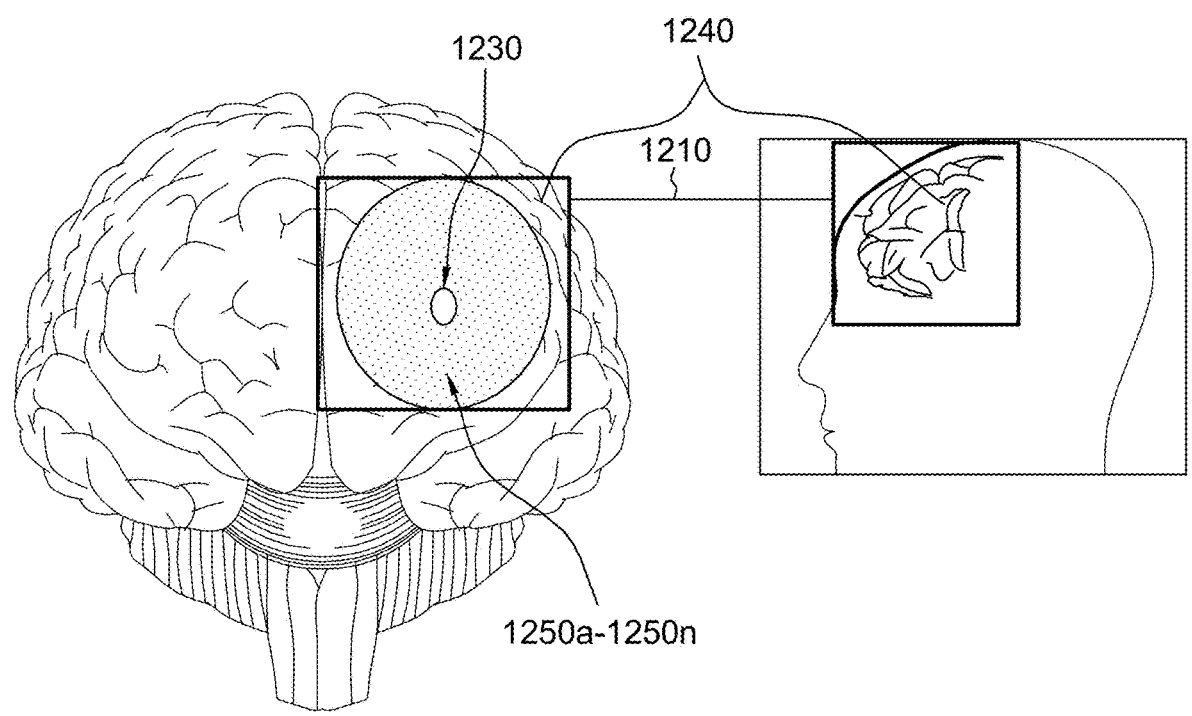
FIG. 12 depicts the creation of multiple detectors from an image, enabling valuable information to be measured concurrently.

FIG. 9 and FIG. 12 illustrate how, in an embodiment of the present invention, by extracting light intensity values from different pixels in the image, many detectors can be created all around a light source insertion point. Unlike traditional head mounted fNIRS systems that include the cost of new photomultiplier tubes for each new detector, in embodiments of the present inventions, detectors may be added by extracting light from different regions of the image, resulting in more detectors per light source (i.e., more regions of the brain and scalp being measured) than could be achieved with head-mounted fNIRS devices. In one example, this approach enables the collection of channels of data in a 3.5 cm radius surrounding the source insertion point. In addition to getting many channel locations of brain data through these source-detector pairings, embodiments of the present invention may also utilize different distances of source-detector pairings to acquire additional information. The additional information acquired may provide value for measurement of cognitive and physiological data.

Referring to FIG. 9, in one aspect, one or more programs take the mean of a 10×10 area of pixels. Using that each pixel is ⅓₃ cm×⅓₃ cm area of the subject. With imaging, one or more programs can take this measurement at 360 degrees of rotation around the source pixels by shirting where the measurement area of interest is situated. FIG. 9 illustrates the 360 degrees of possibilities provided by embodiments of the present invention.

As illustrated in FIG. 12, the information could provide information about connectivity of functional brain regions, the flow of -oxy, -deoxy-, and total hemoglobin over various brain regions, and/or information about the Fast Optical Signal, which has a fast temporal resolution and directly relates to neuronal activation in the brain. This information could also be 'non-cognitive' information, including but not limited to, heartrate and respiration, and/or to remove noise in the cognitive fNIRS signal. Removal of noise can be accomplished by leveraging traditional fNIRS techniques that use a close source-detector pairing (which does not probe into the brain) to get a measure of the noise in the signal. Program code executing on a processor can use this information to adaptively filter out noise from the fNIRS signal, which is acquired by source-detector pairings, for example, with <1 cm of separation between them.

FIG. 9 demonstrates how in embodiments of the present invention, a light source 1230 and image capture device (not pictured) can be utilized as multiple light detectors by using the pixels 1250a-1250n in an image 1210 (captured by the image capture device) as many light detectors. Utilizing the pixels 1250-1250n as multiple detectors enables one or more programs in an embodiment of the present invention to measure large regions of a brain 1240, concurrently, at different depths.

In embodiments of the present invention that track alternating images, the images are tracked such that every odd image has wavelength-1 (e.g., 685 nm) information and every even image has wavelength-2 (e.g., 830 nm) information. The program code saves these image sequences are saved and parses them during processing routines.

In an embodiment of the present invention that includes constant dual source illumination, the optical paths of each wavelength are separated and directed to different imaging devices. Each imager can be set up to be optimized for the wavelength it is responsible for measuring, for example, the optics may be set up to direct the differing wavelength images to separate portions of the imaging surface and saved in different image channels. In dual source illumination, the sources as separated at a distance where the wavelength images of each source can be delineated from one another.

Upon acquiring data during a measurement session, the program code processes the data. To this end, in an embodiment of the present invention, the program code averages each frame of the image using a convolution kernel appropriate for the size of the image. To optimize the relationship between spatial resolution and noise reduction, kernels that represent 0.3 cm$^2$ are used in an embodiment of the present invention. In embodiments of the present invention, the program code may apply strict block averaging and—depending on the conditions and optical properties—Gaussian, Laplacian, or other smoothing or averaging filters may be used. In embodiments of the present invention, the program code can apply these filters, with the 3$^{rd}$ dimension being time, to also gain the benefit of time/frequency filtering. In an embodiment of the present invention, rather than performing a spatial averaging/convolution, one or more programs utilizes the 0.3 cm to optimize between SNR and spatial resolution.

In embodiments of the present invention that utilize alternating sources, after the program code parses the data into independent wavelength series, the program code aligns the data points such that the first odd (e.g., resulting from the 685 nm source) and first even (e.g., resulting from the 830 nm source) are temporally aligned. The program code repeats this process for the 2$^{nd}$ odd and even datapoints and such for the rest of the sequence.

In embodiments of the present invention that utilize constant dual source illumination, generally, interpolation is optional. Each pixel in the image has a distance from the source pixel(s) at the insertion point. $I_1(x,y)$ has the intensity recorded for wavelength 1 (685 nm) and $I_2(x,y)$ has the intensity recorded for wavelength 2 (830 nm). $D(x,y)$ contains the distance of each pixel to the source. Thus, it is possible to have multiple insertion points to measure different locations, and there would be $D_n(x,y)$ which contains the distance information for insertion point n. There is also a $DPF_n(x,y)$ image and a $\varepsilon_n(x,y)$ for the correction coefficients. In an embodiment of the present invention, if any of these items can be estimated as a scalar constant, they can be replaced by one, rather than an image of values.

The program code processes the images point by point to calculate the change in oxy- and deoxy-hemoglobin, for example, in accordance with the equations below. These equations, Equation 1 and Equation 2, represent the Modified Beer-Lambert Law, which is used with traditional fNIRS devices, but is updated for use in embodiments of the present invention based on multiple detection points, as can be created using the pixels surrounding a given light insertion point in an image.

$$dHb(x, y) = \frac{\frac{dI_{685\,nm}(x, y)}{DPF_{685\,nm}(x, y)} * \varepsilon_{830\,nm\,HbO2}(x, y) - \frac{dI_{830\,nm}(x, y)}{DPF_{830\,nm}(x, y)} * \varepsilon_{685\,nm\,HbO2}(x, y)}{\left(\begin{array}{c}\varepsilon_{830\,nm\,HbO2}(x, y) * \varepsilon_{685\,nm\,Hb}(x, y) - \\ \varepsilon_{830\,nm\,Hb}(x, y) * \varepsilon_{685\,nm\,HbO2}(x, y)\end{array}\right) * DPF(x, y)}$$

(Equations 1-2)

$$dHbO_2(x, y) = \frac{\frac{dI_{830\,nm}(x, y)}{DPF_{830\,nm}(x, y)} * \varepsilon_{685\,nm\,HbO2}(x, y) - \frac{dI_{685\,nm}(x, y)}{DPF_{685\,nm}(x, y)} * \varepsilon_{830\,nm\,HbO2}(x, y)}{\left(\begin{array}{c}\varepsilon_{830\,nm\,HbO2}(x, y) * \varepsilon_{685\,nm\,Hb}(x, y) - \\ \varepsilon_{830\,nm\,Hb}(x, y) * \varepsilon_{685\,nm\,HbO2}(x, y)\end{array}\right) * DPF(x, y)}$$

Figure 11:
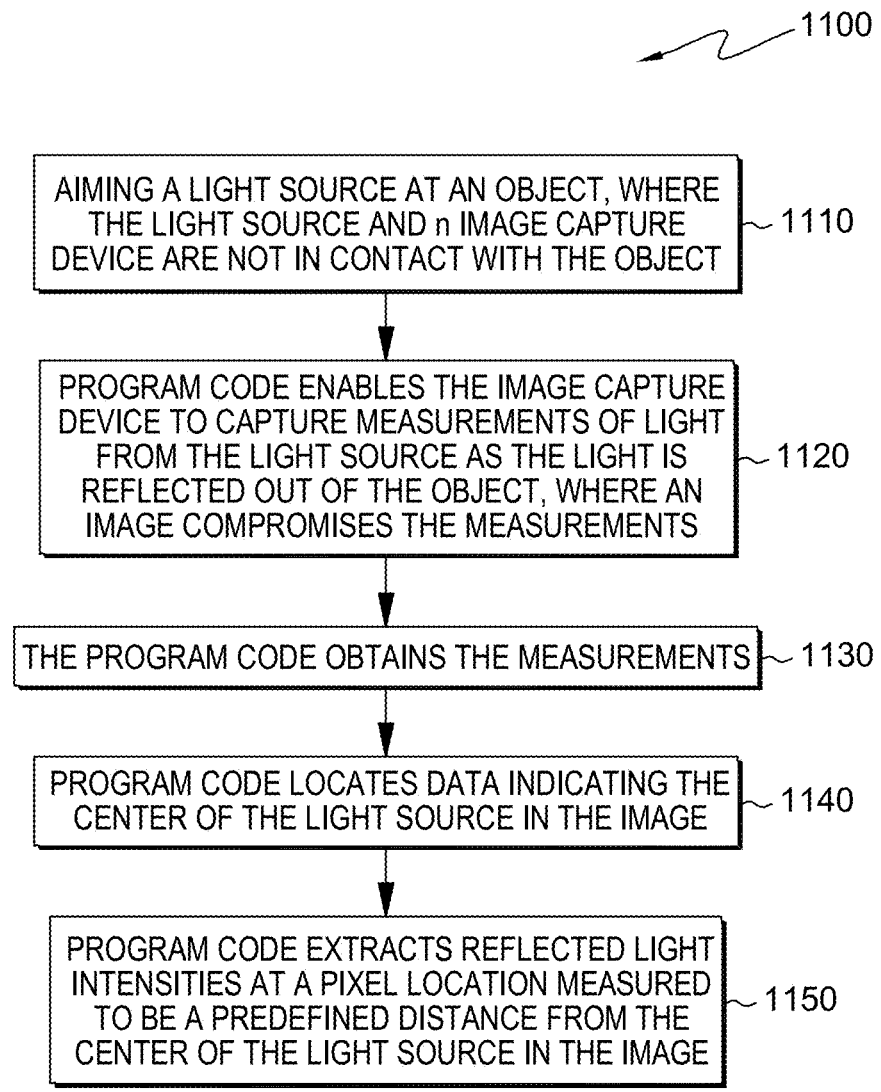
FIG. 11 is a workflow 1100 of an embodiment of the present invention.

FIG. 11 is a workflow 1100 of an embodiment of the present invention. As depicted in FIG. 11, in an embodiment of the present invention, program code executing on a processor, aims a light source at an object, where the light source is positioned a pre-defined distance from the image capture device and both the image capture device and the light source are positioned at a distance from the object (1110). The program code enables the image capture device to capture measurements of light from the light source as the light is reflected out of the object, where an image comprises the measurements (1120). The program code obtains the measurements (1130). The program code locates data indicating the center of the light source in the image (1140). The program code extracts reflected light intensities at a pixel location measured to be a predefined distance from the center of the light source in the image (1150).

Different types and configurations of light sources may be utilized in embodiments of the present invention (to assist in collecting fNIRS data without utilizing an apparatus that makes direct contact with a subject). In one embodiment of the present invention, the light source includes alternating coherent light sources, for example, two light sources, one source that emits at 685 nm and the other that emits at 830 nm. In another embodiment of the present invention, the light source may comprise one dual band coherent light source, which is continually illuminated. When utilizing a dual band coherent light source, light of more than one wavelength, e.g. 685 nm and 830 nm, may be coupled together into the same optical path.

In an embodiment of the present invention that utilizes alternating method coherent light sources, the embodiment may include a frame-to-wavelength synchronization device that alternates the coherent light sources such that only one wavelength is present in a given image. After the images are collected (each frame alternates what information it carries) the frames are sorted and processed to create the fNIRS signals. In this embodiment of the present invention, the image capture device may comprise a single camera. This method is illustrated in FIG. 4.

In an embodiment of the present invention that utilizes a continually illuminating light source, the image capture device may comprise two cameras that aquire the images. The embodiment may include a dichroic mirror setup that splits the optical paths such that 685 nm light and 830 nm light information go to their respective camera. The mirror removes a need for a frame-to-wavelength synchronization device. In this embodiment of the present invention, the images from each camera are independently processed to gain raw light intensity images and then processed to create the fNIRS signals. This method is illustrated in FIG. 5.

Figure 10:
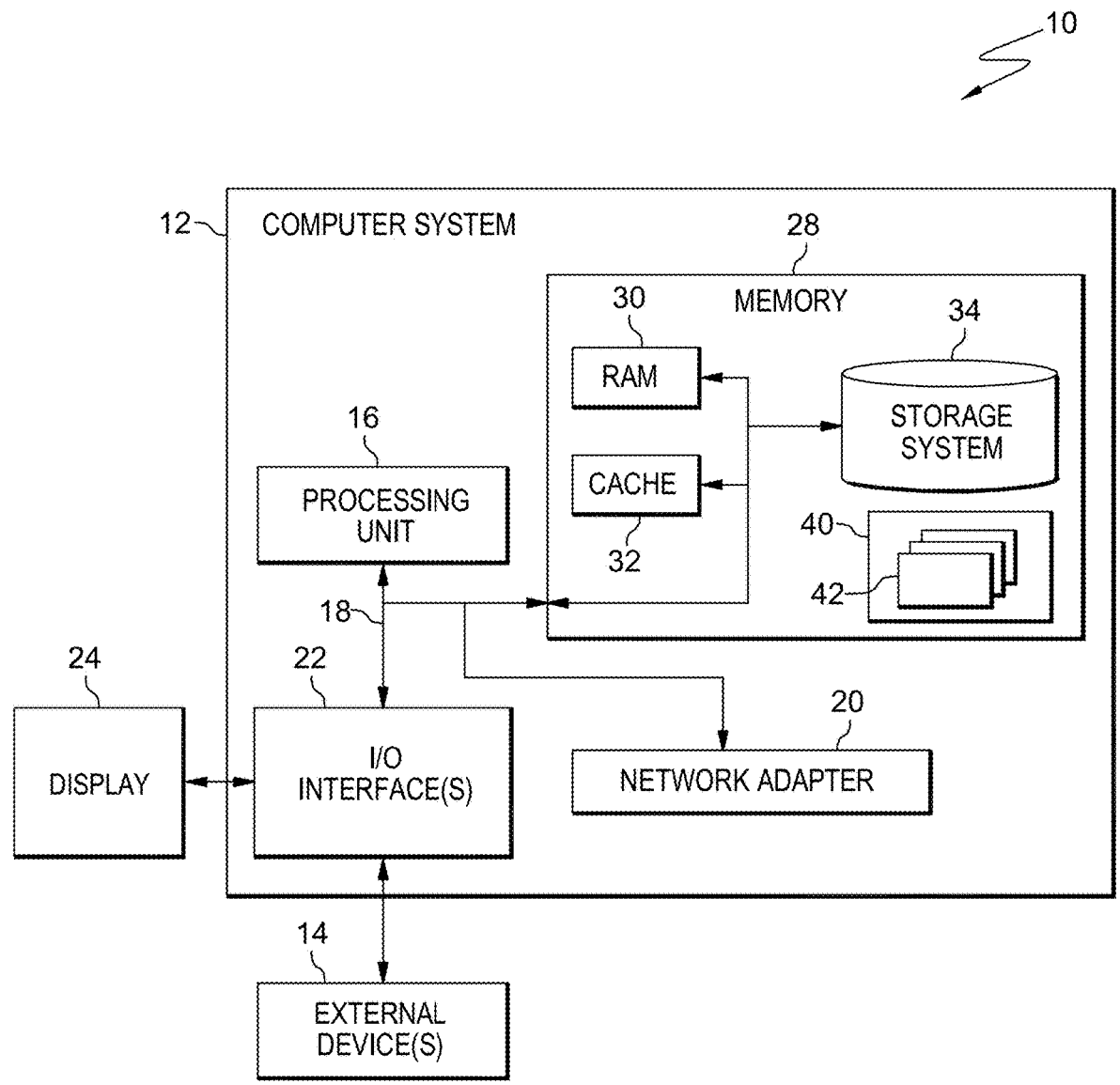
FIG. 10 depicts a hardware overview of a computing node, in accordance with one or more aspects of the present invention.

FIG. 10 depicts a hardware overview of a computing node, in accordance with one or more aspects of the present invention. For example, this hardware node may comprise a portion of the program code and/or the processor upon which the program code executes. FIG. 10 depicts a hardware overview of a computing node 10, in accordance with one or more aspects set forth herein.

Program/utility 40 can include one or more program 42 (e.g., program code), and program/utility 40, including, for example, one or more program 440 to obtain and process fNIRS data from a captured image. Program/utility 40 as set forth can optionally include additional programs 42.

One or more program 42 can have a set (at least one) of program modules, and may be stored in memory 28 by way of example, and not limitation, as well as an operating system, one or more application programs, other program modules, and program data. Each of the operating system, one or more application programs, other program modules, program data, and one or more program, or some combination thereof, may include an implementation of a networking environment. One or more program 42 generally carry out the functions and/or methodologies of embodiments of the invention as described herein.

Referring again to FIG. 10:

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A computer-implemented method, comprising:
aiming a light source at an object, wherein the light source is communicatively coupled to one or more processors, wherein the light source is positioned at a predefined distance from the object such that the light source and an image capture device are not in direct contact with the object, the image capture device comprising at least two cameras;
enabling, by the one or more processors, the image capture device, to capture measurements of reflected light, wherein the reflected light comprises the light from the light source as the light is reflected out of the object, wherein the image capture device is communicatively coupled to the processor, and wherein an image from each camera comprises the measurements;
obtaining, by the one or more processors, from the image capture device, the images from each camera;
locating, by the one or more processors, in each image, data indicating a center of the light source in each image; and
extracting, by the one or more processors, intensities of the reflected light at a pixel location measured to be a predefined distance from the center of the light source in each image, wherein the extracting comprises:
extracting images from each camera independently to gain raw light intensity images; and processing the raw light intensity images to create Functional Near-Infrared Spectroscopy (fNIRS) signals.

2. The method of claim 1, wherein the object is a portion of a head of an individual, further comprising:
utilizing, by the one or more processors, the intensities of the reflected light to determine total blood flow in a brain of the individual.

3. The method of claim 1, wherein the object is a portion of a head of an individual, further comprising:
utilizing, by the one or more processors, the intensities of the reflected light to determine a change in oxygen in blood flow in a brain of the individual.

4. The method of claim 1, wherein the light source emits two wavelengths.

5. The method of claim 4, wherein a first wavelength of the two wavelengths comprises about 685 nm and a second wavelength of the two wavelengths comprises about 830 nm.

6. The method of claim 4, wherein the light source comprises coherent light sources, and wherein the aiming comprises:
performing, by the one or more processors, frame-to-wavelength synchronization to alternate the coherent light sources such that one wavelength of the two wavelengths is present in each image captured by the image capture device.

7. The method of claim 6, wherein the method further comprises:
obtaining, by the one or more processors, from the image capture device, additional images, wherein the images from each camera and the additional images each comprise one wavelength of the two wavelengths.

8. The method of claim 1, wherein the aiming further comprises:
determining, by the one or more processors, that the image capture device is acquiring a series of images of reflected light of the light source off the object; and
based on this determining, utilizing, by the one or more processors, a synchronization controller to alternate wavelengths produced by the light source.

9. The method of claim 1, the method further comprising:
splitting, with a dichroic mirror, an optical path of the reflected lights into two optical paths, such that each optical path of the two optical paths provides light information to one camera of the at least two cameras.

10. The method of claim 1, wherein the object comprises a portion of a head of a human, and the aiming further comprises:
applying the light source at an insertion point, wherein the insertion point comprises an area where a sufficient distance between a point of innervation into tissue of the object and a maximum distance to measure a depth of cortical tissue of the object to measure.

11. A computer program product comprising:
a computer readable storage medium readable by one or more processors, and storing instructions for execution by the one or more processors for performing a method comprising:
aiming a light source at an object, wherein the light source is communicatively coupled to one or more processors, wherein the light source is positioned at a predefined distance from the object such that the light source and an image capture device are not in direct contact with the object, the image capture device comprising two cameras;
enabling, by the one or more processors, the image capture device, to capture measurements of reflected light, wherein the reflected light comprises the light from the light source as the light is reflected out of the object, wherein the image capture device is communicatively coupled to the processor, and wherein an image from each camera comprises the measurements;
obtaining, by the one or more processors, from the image capture device, the images from each camera;
locating, by the one or more processors, in each image, data indicating a center of the light source in each image; and
extracting, by the one or more processors, intensities of the reflected light at a pixel location measured to be a predefined distance from the center of the light source in each image, wherein the extracting comprises:
extracting images from each camera independently to gain raw light intensity images; and
processing the raw light intensity images to create Functional Near-Infrared Spectroscopy (fNIRS) signals.

12. The computer program product of claim 11, wherein the object is a portion of a head of an individual, further comprising:
utilizing, by the one or more processors, the intensities of the reflected light to determine total blood flow in a brain of the individual.

13. The computer program product of claim 11, wherein the object is a portion of a head of an individual, further comprising:
utilizing, by the one or more processors, the intensities of the reflected light to determine a change in oxygen in blood flow in a brain of the individual.

14. A system comprising:
a memory;
a processor in communication with the memory;
a light source in communication with the processor;
an image capture device in communication with the processor, wherein the light source and the image capture device are not in direct contact with an object, the image capture device comprising two cameras; and
program instructions executable by the one or more processor via the memory to perform a method, the method comprising:
aiming the light source at the object;
enabling, by the one or more processors, the image capture device, to capture measurements of reflected light, wherein the reflected light comprises the light from the light source as the light is reflected out of the object, and wherein an image from each camera comprises the measurements;
obtaining, by the one or more processors, from the image capture device, the images from each camera;
locating, by the one or more processors, in each image, data indicating a center of the light source in each image; and
extracting, by the one or more processors, intensities of the reflected light at a pixel location measured to be a predefined distance from the center of the light source in each image, wherein the extracting comprises:
extracting images from each camera independently to gain raw light intensity images; and
processing the raw light intensity images to create Functional Near-Infrared Spectroscopy (fNIRS) signals.

15. The system of claim 14, wherein the light source emits two wavelengths.

16. The system, of claim 15, wherein a first wavelength of the two wavelengths comprises about 685 nm and a second wavelength of the two wavelengths comprises about 830 nm.

17. The system of claim 15, wherein the light source comprises coherent light sources, and wherein the aiming comprises:
   performing, by the one or more processors, frame-to-wavelength synchronization to alternate the coherent light sources such that one wavelength of the two wavelengths is present in each image captured by the image capture device.

18. The system of claim 17, wherein the method further comprises:
   obtaining, by the one or more processors, from the image capture device, additional images, wherein the images from each camera and the additional images each comprise one wavelength of the two wavelengths.

* * * * *